United States Patent
Boni et al.

(10) Patent No.: US 6,544,549 B1
(45) Date of Patent: Apr. 8, 2003

(54) MULTILAMELLAR COALESCENCE VESICLES (MLCV) CONTAINING BIOLOGICALLY ACTIVE COMPOUNDS

(75) Inventors: Lawrence T. Boni, Monmouth Junction, NJ (US); Michael M. Batenjany, Hamilton, NJ (US); Stella Gevantmakher, Plainsboro, NJ (US); Mircea C. Popescu, Plainsboro, NJ (US)

(73) Assignee: Biomira USA Inc., Cranbury, NJ (US)

( * ) Notice: Subject to any disclaimer, the term of this patent is extended or adjusted under 35 U.S.C. 154(b) by 359 days.

(21) Appl. No.: 09/164,350

(22) Filed: Oct. 1, 1998

Related U.S. Application Data

(60) Provisional application No. 60/060,606, filed on Oct. 1, 1997.

(51) Int. Cl.$^7$ ............................................. A61K 9/127
(52) U.S. Cl. ........................ 424/450; 264/4.1; 264/4.3
(58) Field of Search ................................ 424/450, 1.21, 424/9.321, 9.51, 417, 94.3; 264/4.1, 4.3, 4.6; 436/829; 935/54

(56) References Cited

FOREIGN PATENT DOCUMENTS

| JP | 4-356421 | 12/1992 |
|---|---|---|
| WO | WO 97/29769 | 8/1997 |

OTHER PUBLICATIONS

M.J. Poznansky et al., "Pharmacological Reviews" vol. 36 No. 4, *Biological Approaches to the Controlled Delivery of Drugs: A Critical Review*, pp. 277–336, (1984).

B.E. Ryman et al., "Essays in Biochemistry" vol. 16, *Lipsomes—Bags of Potential*, pp. 49–99, (1980).

G. Weissmann et al., "Liposomes in Biological Systems", *Uptake of Enzyme–bearing Liposomes by cell in vivo and in vitro*, pp. 153–179, (1980).

G.Lopez–Berestein, "Annals of Internal Medicine" vol. 105 No. 1, *Liposomal Amphotericin B in the Treatment of Fungal Infections*, pp. 130–131, (Jul. 1986).

H.H. Hsieh et al., "Transplantation Proceedings" vol. XVII No. 1, *Preliminary Report: The Use of Liposome–Encapsulated Cyclosporine in a Rat Model*, pp. 1397–1400, (1985).

A. Rahman et al., "Cancer Research" vol. 42, *Doxorubicin–induced Chronic Cardiotoxicity and Its Protection by Liposomal Administration*, pp. 1817–1825, (May 1982).

E.A. Forssen et al., "Cancer Research" vol. 43, *Improved Therapeutic Benefits of Doxorubicin by Entrapment in Anionic Liposomes*, pp. 546–550, (Feb. 1983).

A.D. Bangham et al., "Methods in Membrane Biology" vol. 1, *Preparation and Use of Liposomes as Models of Biologocal Membranes*, pp. 1–69, (1974).

(List continued on next page.)

*Primary Examiner*—Gollamudi S. Kishore
(74) *Attorney, Agent, or Firm*—Foley & Lardner

(57) ABSTRACT

A method for producing multilamellar coalescence vesicles (MLCVs) containing increased amounts of biologically active compound is disclosed. The method involves hydrating at least one powdered lipid in an aqueous buffer at a temperature above the phase transition temperature of the highest melting lipid to form multilamellar vesicles, reducing the size of the multilamellar vesicles to about 20–400 nm to produce small unilamellar vesicles (SUVs) or large unilamellar vesicles (LUVs) or a mixture thereof; and incubating the SUVs, LUVs or mixture thereof with a biologically active compound in an aqueous solution under sufficient conditions to form MLCVs containing the biologically active compound without the use of an organic solvent, a freeze-thawing step or a dehydration step. MLCVs produced by this method contain increased amounts of biologically active compound over prior art liposomes produced with an organic solvent, a freeze-thawing step or a dehydration step and fewer vesicles are substantially free of biologically active compound

20 Claims, 14 Drawing Sheets

OTHER PUBLICATIONS

D. Gingell et al., "Membrane Fusion" vol. 15, *Problems in the Physical Interpretation of Membrane Interaction and Fusion*, pp. 791–833, (1978).

F.C. Szoka, "Lipid Vesicles" Ch. 10, *Model Systems to Study Membrane–Membrane Destabilization and Fusion*, pp. 209–240, (1987).

S. Nir et al., "Biochimica et Biophysica Acta" vol. 688, *The Rate of Fusion of Phospholipid Vesicles and the Role of Bilayer Curvature*, pp. 275–278, (1982).

A. Jackson, "Drug Metabolism and Disposition" vol. 9 No. 6, *Intramuscular Absorption and Regional Lymphatic Uptake of Liposome–Entrapped Inulin*, pp. 535–540, (1981).

P. Anderson, "Clin. Pharmacokinet." vol. 27 (1), *Effects of Route and Formulation on Clinical Pharmacokinetics of Interleukin–2*, pp. 19–31, (1994).

C.F. Schmidt, "Biochemistry" vol. 20 (16), *Vesicle–Vesicle Interactions in Sonicated Dispersions of Dipalmitoylphosphatidylcholine*, pp. 4792–4797, (1981).

A.L. Larrabee, "Changes in Vesicle Size Distribution" vol. 18 No. 15, *Time–Dependent Changes in the Size Distribution of Distearoylphosphatidylcholine Vesicles*, pp. 3321–3326, (1979).

S.E. Schullery et al., "Biochemistry" vol. 19, *Fusion of Dipalmitoylphosphatidylcholine Vesicles*, pp. 3919–3923, (1980).

N.O. Petersen et al., "Biochimica et Biophysica Acta" vol. 509, *The Effects of the Thermal Prephase Transition and Salts in the Coagulation and Flocculation of Phosphatidylcholine Bilayer Vesicles*, pp. 111–128, (1978).

M. Wong et al., "Biochemistry" vol. 21, *Fusion of Dipalmitoylphosphatidylcholine Vesicles at 4° C*, pp. 4126–4132, (1982).

D.S. McConnell et al., "Biochimica et Biophysica ACTA" vol. 818, *Phospholipid vesicle fusion and drug loading: temperature, solute and cholesterol effects, and, a rapid preparation for solute–loaded vesicles*, pp. 13–22, (1985).

B.P. Gaber, "Biochimica et Biophysica ACTA" vol. 685, *Kinetic and Thermodynamic Studies of the Fusion of Small Unilamella Phospholipid Vesicles*, pp. 87–93, (1982).

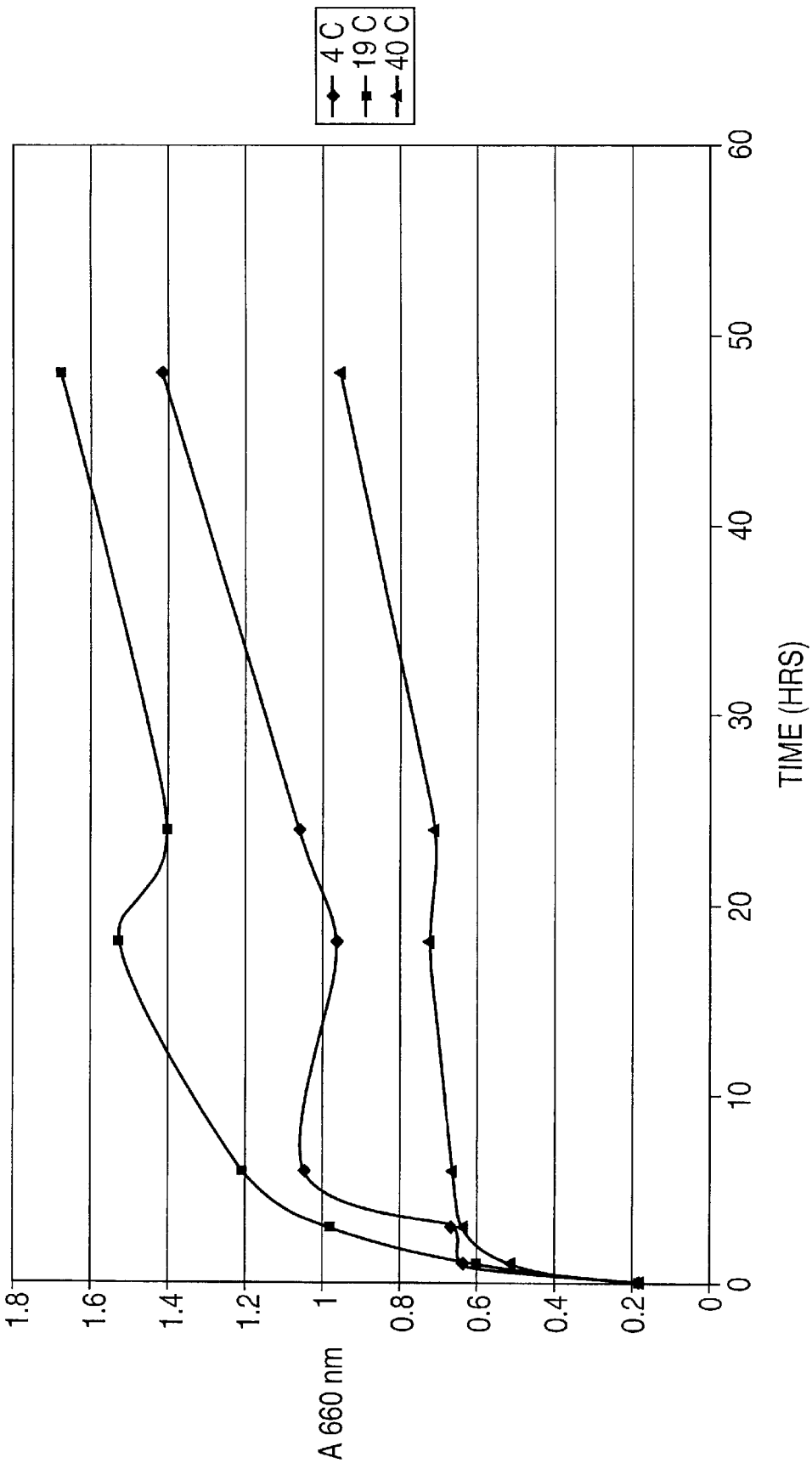

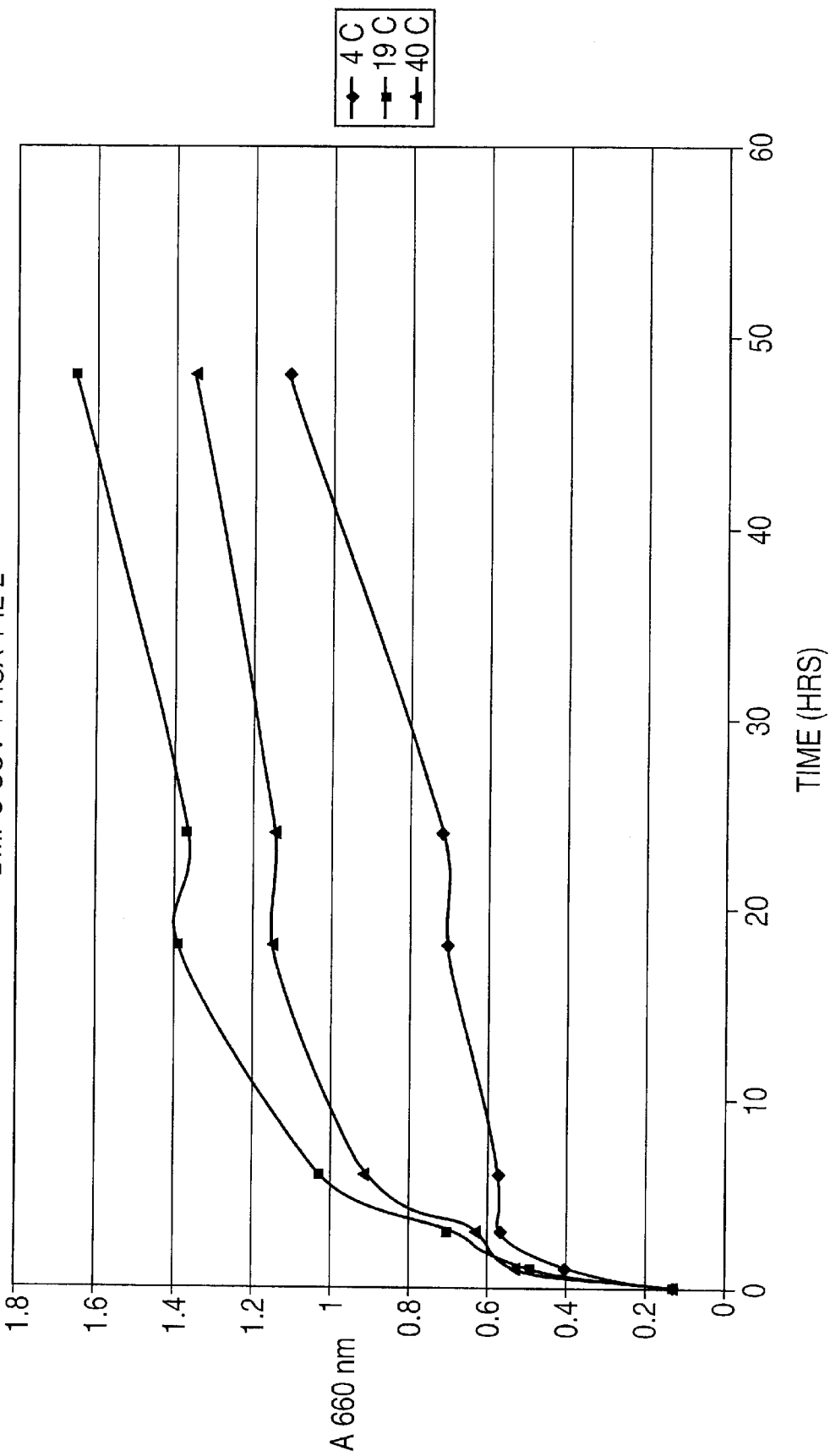

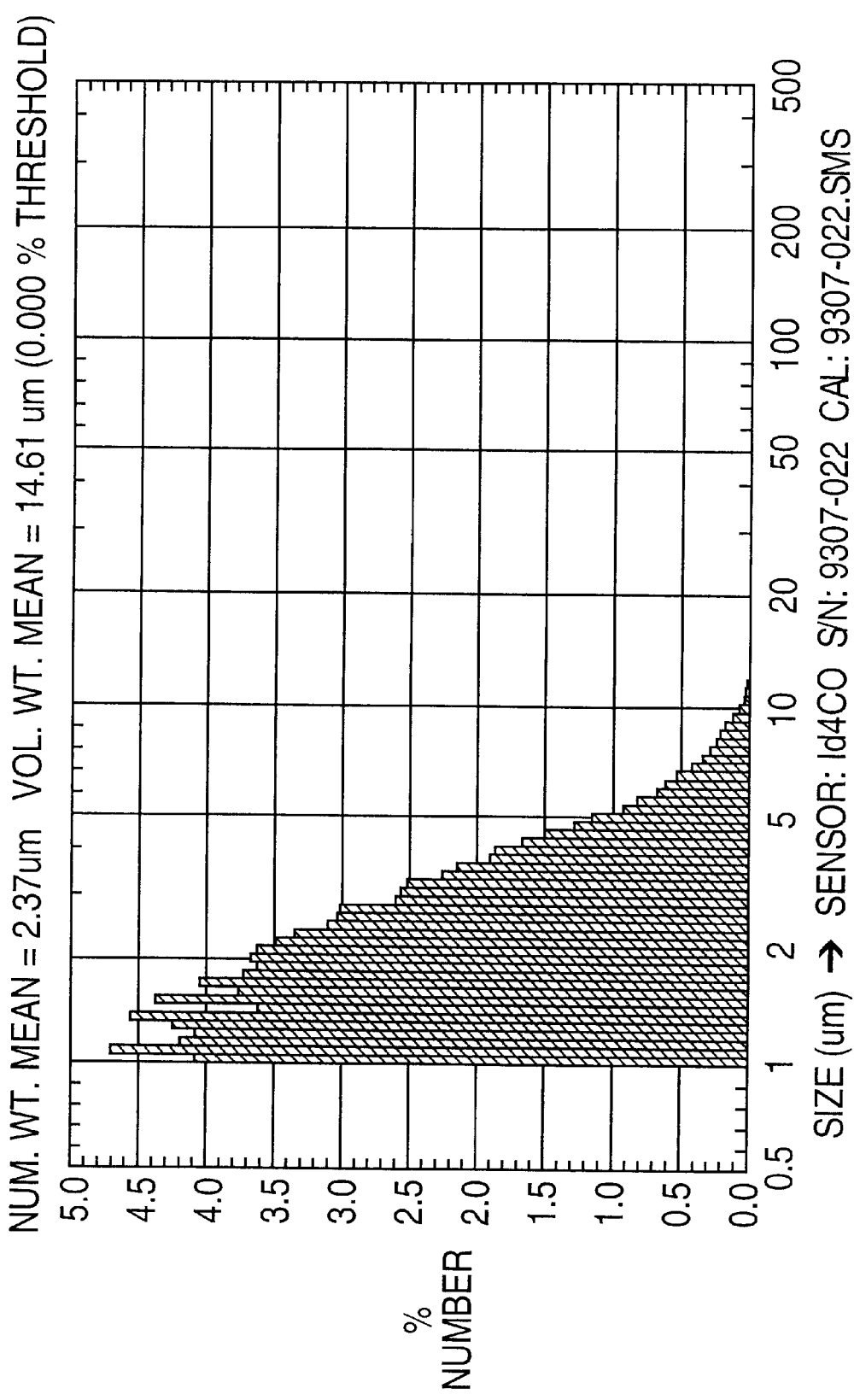

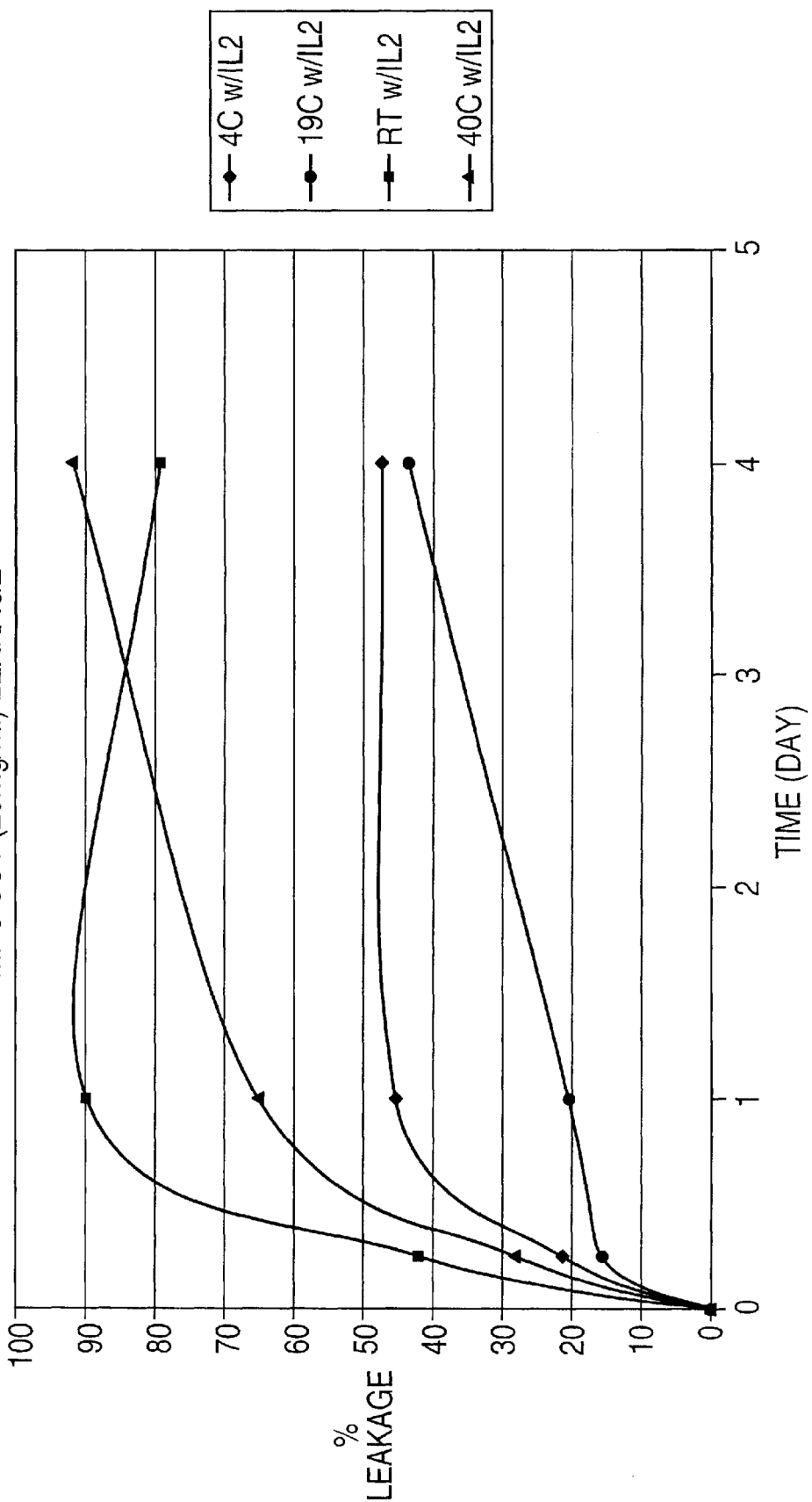

COALESCENCE KINETICS, DMPC/IL-2 19C

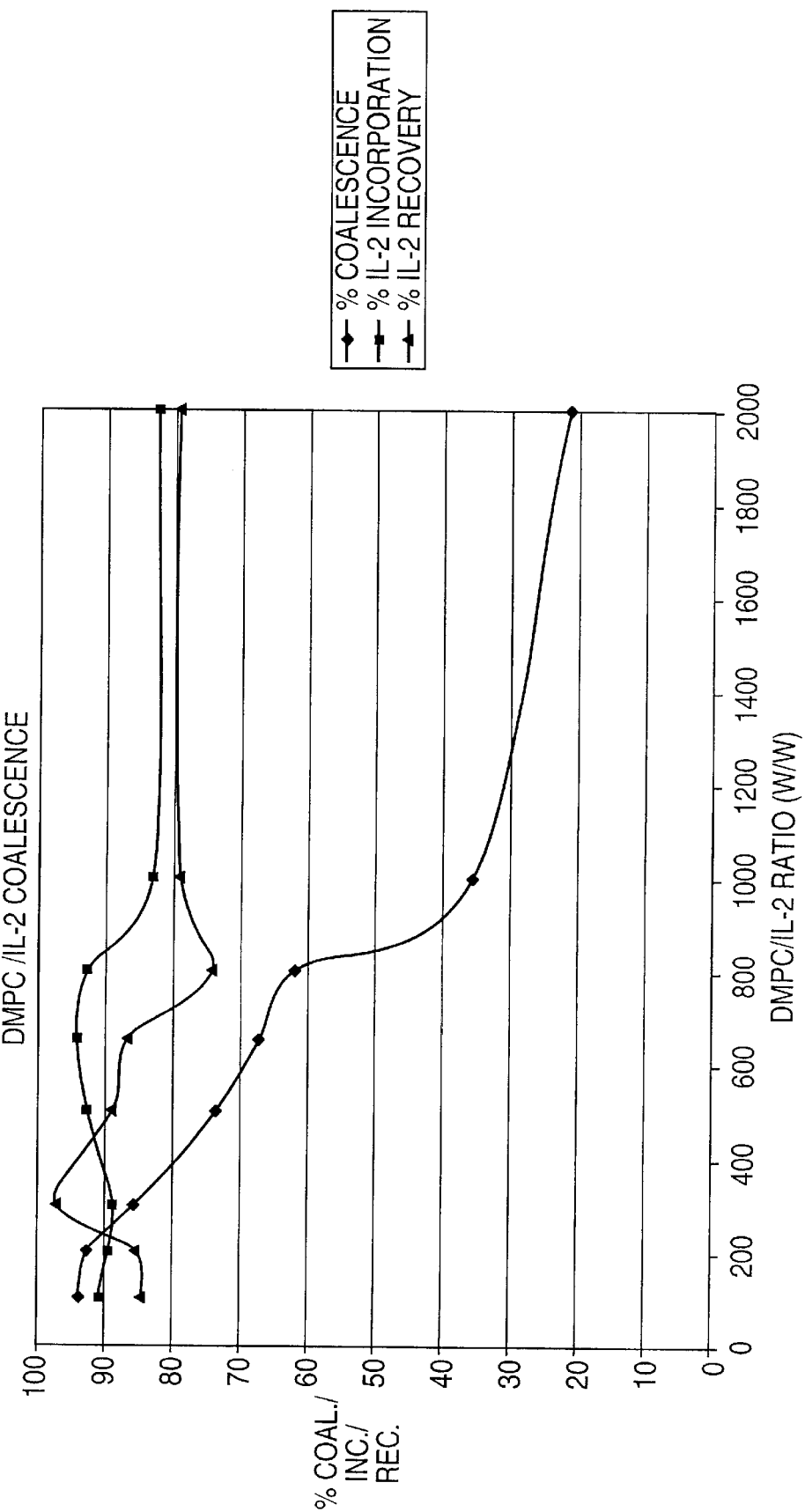

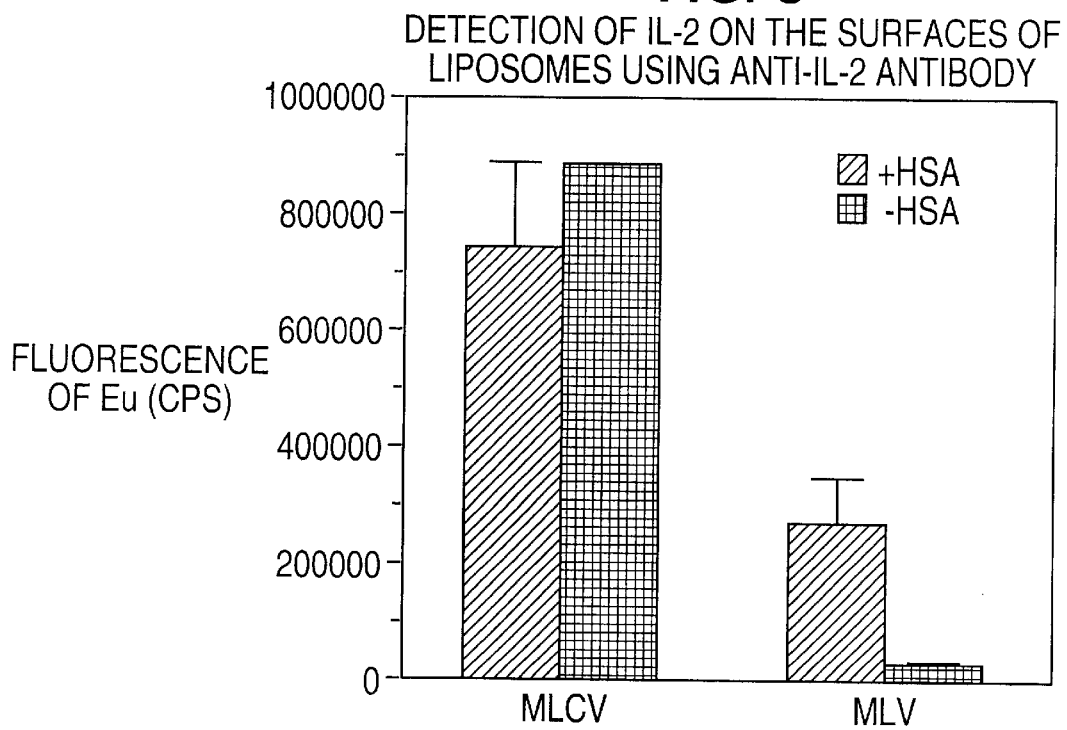

MULTILAMELLAR COALESCENCE VESICLES (MLCV) CONTAINING BIOLOGICALLY ACTIVE COMPOUNDS

This application is a continuation-in-part of the provisional application, U.S. Ser. No. 60/060,606 filed on Oct. 1, 1997, which is incorporated in its entirety by reference.

BACKGROUND OF THE INVENTION

The present invention is directed to a method of producing multilamellar coalescence vesicles (MLCVs) which contain a high incorporation of biologically active compounds, using small unilamellar vesicles (SUVs) and large unilamellar vesicles (LUVs) without steps involving multiple freeze-thawing cycles, using organic solvents or dehydration of the vesicles.

The present invention also is directed to the MLCVs produced by the present method. These MLCVs possess advantageous properties of containing higher amounts of surface and total biologically active compounds, without the use of human serum albumin (HSA), as compared to prior art multilamellar vesicles (MLVs).

Liposomes are known to be useful as carriers of biologically active compounds which facilitate the delivery of these compounds to the body. Liposomes have been evaluated as potential drug delivery systems to introduce biologically active compounds into cells. See Poznansky and Juliano, *Pharmacol. Rev.* 36, 277–336 (1984); B. E. Ryman et al., *Essays in Biochemistry*, 16, 49 (1980). Several routes of administration have been used for the administration of liposomes, for example, intravenous, subcutaneous, intraperitoneal, and oral delivery. See Gregoriadis and Allison, eds., *Liposomes in Biological Systems*, John Wiley & Sons, New York (1980) at pages 153–178. An important advantage of liposomal delivery is the change in tissue distribution and binding properties as compared to the free forms of the bioactive ingredient, resulting in an enhanced therapeutic index and decreased toxicity. For example, decreased nephrotoxicity has been associated with the use of liposomes containing amphotericin B or cyclosporin A. See G. Lopez-Berestein, *Ann. Int. Med.*, 105, 130 (1985) and Hsieh et al., *Transplantation Proceedings*, Vol. XVII, 1397–1400 (1985). Also, reduced cardiotoxicity and nephrotoxicity are associated with liposomes containing doxorubicin and cisplatin, respectively, as compared to the free forms of the drugs. See Rahman et al., *Cancer Res.*, 42, 1817 (1982); and Forssen et al., *Cancer Res.*, 43, 546 (1983).

It is known that, under appropriate conditions, phospholipid dispersions can spontaneously reform, in the presence of water, into closed membrane systems. Electron microscopy reveals that these closed structures are made of a number of concentric bilayers or lamellae composed of phospholipid molecules, and are known as liposomes. The usefulness of liposomes as a model membrane system arises from the fact that, as the dry phospholipids undergo a defined sequence of molecular rearrangements, there is an opportunity for an unrestricted entry of hydrophilic solutes into the interlamellae space. Similarly, sequestration of hydrophobic solutes occurs within the hydrophobic bilayers. The result is a delivery system that can contain varying amounts of cytokines or other biologically active compounds, depending on the type of interaction between the solute and the phospholipid assembly.

Many methods have been proposed for the preparation of liposomes. The classical method of making prior art liposomes, MLVs containing a biologically active compound, is to mix a lipid in an organic solvent, remove the solvent from the solution, leaving a residue, suspend the residue in a buffer containing a biologically active compound, agitate and homogenize the suspension until the MLVs which contain the biologically active compound are formed, and isolate the resulting MLVs. See Bangham et al. (1974) In *Methods in Membrane Biology* (Korn, E., ed.), pp 1–68, Plenum Press, N.Y.

One of the most widely used techniques is known as the thin film method, which involves the aqueous hydration of a dried lipid film. See Bangham et al. Briefly, lipids of the desired composition, in solution with an organic solvent, are dried in the form of a thin film on the walls of a round-bottomed flask. A biologically active compound can be included in the film at this stage. The dry film is hydrated by adding a suitable aqueous phase and gently swirling the flask. With a hydrophilic biologically active compound, an aqueous solution containing the biologically active compound is used for hydration. MLVs are formed by this procedure.

Although MLVs are produced and used in medical applications, a major problem in the manufacture of MLVs is the use of organic solvents to dissolve the lipids. Further, many biologically active compounds are incompatible with organic solvents, and the removal of organic solvents from these preparations is difficult and tedious. Additionally, to form MLVs with high entrapment of biologically active compound, the solution must be subjected to repeated freeze-thawing cycles. Large scale freeze-thawing is difficult to carry out, especially under sterile conditions. Further, to produce MLVs under sterile conditions, it is necessary to sterilize the lipid prior to placing it into solution. This sterilization process may result in the breakdown of the lipids, resulting in the formation of by-products.

The process of the present invention provides a method of producing MLCVs, which has none of the limitations of the prior art methods, and several advantages over the prior art methods. The process of the present invention allows the improved entrapment of solutes. These solutes can be biologically active compounds or any compound, such as HSA, mannitol, or glycerol, which can be entrapped by the liposomes, MLCVs, of the present invention. Examples of additional biologically active compounds useful in the present invention are pharmaceutical peptides, proteins, antigens and drugs or any biologically active compound that can be incorporated into a liposome for delivery to a subject.

The present process results in the production of MLCVs without the use of organic solvents while supplying the means for sterilizing the lipid in an aseptic process by filter sterilization. The process of the present invention can be used easily to produce a small scale production run as well as a large production run while maintaining a simple manufacturing scheme. Moreover, the MLCVs of the present invention are unique structurally in that they possess a varying degree of partially coalesced vesicles in addition to numerous lamellae. Further, the present method produces MLCVs that possess a consistent size and consistent distribution of biologically active compound with less variability than obtained using the prior art methods.

MLCVs made by the method of the present invention contain a greater amount of biologically active compound as a result of enhanced entrapment. The present MLCVs possess a greater amount of surface biologically active compound and exhibit a greater recovery of biologically active compound than the prior art MLVs. Therefore, the present method results in enhanced recovery and incorporation of biologically active compounds as compared to the prior art. In regard to the present invention, the term recovery is defined as the percent of output over input; that is, the amount of the biologically active compound that is present in products and unreacted starting materials with the remainder being lost in processing. The term incorporation as used in the present invention is defined as the percent of output that is entrapped in liposomes and is no longer free.

The process of the present invention is referred to as a coalescence process because the produced MLCVs are produced as a result of rupturing and resealing of bilayers accompanied by leakage of internal contents. This process differs from vesicle fusion in which the combining of vesicles is accompanied by the mixing of internal contents with no or minimal leakage. See Gingell, D. and Ginsberg, L. (1978), In: *Membrane Fusion* (Poste, G. & Nicolson, G. L., eds.), pp.791–833, Elsevier/North-Holland Biomedical Press, NY.; Szoka, F. (1987), In: *Cell Fusion* (Sowers, A. E., ed.), pp. 209–240, Plenum Press, NY; Nir, S., Wilschut, J. and Bentz, J. (1982), *Biochim. Biophys. Acta* 688:275–278; Poste, G and Nicolson, G. L. (1978) Membrane Fusion, Elsevier/North-Holland Biomedical Press, NY.

Further, the MLCVs of the present invention have sizes (average diameters) of about 1000 to 5000 nm. However, the average size of the MLCVs of the present invention may be as small as at least about 100 nm or greater; e.g., at least 200 nm or greater. Prior art methods which use fusion of SUVs below the phase transition temperature result in unilamellar vesicles having average diameters of less than 100 nm. Liposomes of an average diameter greater than 100 nm have a greater accumulation in the lung, liver, spleen and lymph nodes than smaller liposomes. These liposomes with an average diameter greater than 100 nm are often used to target organs for prophylactic and therapeutic treatment. See Jackson (1981), *Drug Med. Disp.* 9: 535–540.

SUMMARY OF THE INVENTION

The method of the present invention is directed to producing multilamellar coalescence vesicles (MLCVs) containing a biologically active compound by hydrating at least one powdered lipid in an aqueous buffer at a temperature above the phase transition temperature of the highest melting lipid to form multilamellar vesicles (MLVs), reducing the size of the MLVs to about 20–400 nm to produce small unilamellar vesicles (SUVs) or large unilamellar vesicles (LUVs) or a mixture thereof, and incubating the SUVs, LUVs or mixture thereof with at least one biologically active compound in an aqueous solution under sufficient conditions to form MLCVs containing said at least one biologically active compound. The method of the present invention is performed without the use of an organic solvent, a freeze-thawing step or a dehydration step. The size reducing step of the method comprises exposing the MLVs to a high shear force which is effected by one or more of sonication, homogenization or extrusion. The method further includes sterile filtering the SUVs, LUVs or mixture thereof prior to mixing the SUVs, LUVs or mixture thereof with the biologically active compound(s).

The method of the present invention discloses the production of MLCVs containing increased amounts of biologically active compounds. These MLCVs have an average diameter of at least 100 nm or greater, preferably in the range of 1000 to 5000 nm, and are produced without the use of steps involving freeze-thawing, organic solvents or dehydration.

The method of the present invention includes the steps of hydrating powdered lipid(s) with an appropriate buffer in a temperature jacketed mixing vessel at a temperature above the phase transition temperature of the highest melting lipid. Then, the size of the vesicles is reduced from the micron range to about a 20–400 nm range. These vesicles are small unilamellar vesicles (SUVs) or large unilamellar vesicles (LUV) or a mixture thereof, and are produced by known standard methods that utilize high shearing forces, such as sonication, homogenization or extrusion. Homogenizers particularly useful in the present invention are high pressure homogenizers, such as those manufactured by Gaulin Rannie or Microfluidics. This latter step is also carried out at a temperature above the phase transition temperature of the lipid mixture. The resulting SUVs and/or LUVs are then sterile filtered into a mixing vessel which is also maintained at a temperature above the phase transition temperature of the highest melting lipid. The biologically active compound (s) and any necessary excipients are added through a sterilizing filter and mixed while dropping the temperature to the phase transition temperature of the highest melting lipid, or maintaining the temperature, preferably between the pretransition and main transition temperature range. The incubation may also be performed below the pretransition, below the subtransition or above the main transition temperature of the lipid system. Then, the mixture is incubated for a period of time from minutes up to days. During this time the SUVs and/or LUVs are coalesced to form larger vesicles, MLCVs, which are generally have about 100 nm or greater average diameter.

BRIEF DESCRIPTION OF THE DRAWINGS

FIGS. 1A and 1B are graphical depictions of the effect of temperature on the coalescence of dimyristoyl phosphatidylcholine (DMPC) SUVs with interleukin-2 (IL-2), with and without HSA. The designations 4C, 19C and 40C represent samples run at 4° C., 19° C. and 40° C., respectively.

FIG. 3 is a graphical depiction of the size distribution of the coalescence products produced by the method of the present invention, as applied to DMPC liposomes containing IL-2. Analysis was performed using a PSS 770 Accusizer system.

FIG. 4 is a graphical depiction of the leakage of an entrapped quenched fluorescent dye (ANTS) from DMPC SUVs in the presence of IL-2 over time at 4° C. (diamond), 19° C. (circle), room temperature (20–24° C.) (square) and 40° C. (triangle).

FIG. 7 is a graphical depiction of the effect of varying the DMPC/IL-2 ratio on the rate of DMPC SUV coalescence for the range of 50/1 to 2000/1 (w/w—mass ratio).

FIG. 9 is a graphical depiction of the differences in surface bound IL-2 found in MLCVs and MLVs containing IL-2, with and without HSA, as formed by the process described in Anderson, P. M. and Sorenson, M. A. (1994), *Clin. Pharmacokinet.* 27 (1): 19–31. The bars and lines represent the means and standard deviations of results based on the testing of three independently processed liposomal preparations with the exception of the MLCV formulation processed without HSA which represents the result based on a single preparation.

DETAILED DESCRIPTION OF THE INVENTION

Figure 2A:
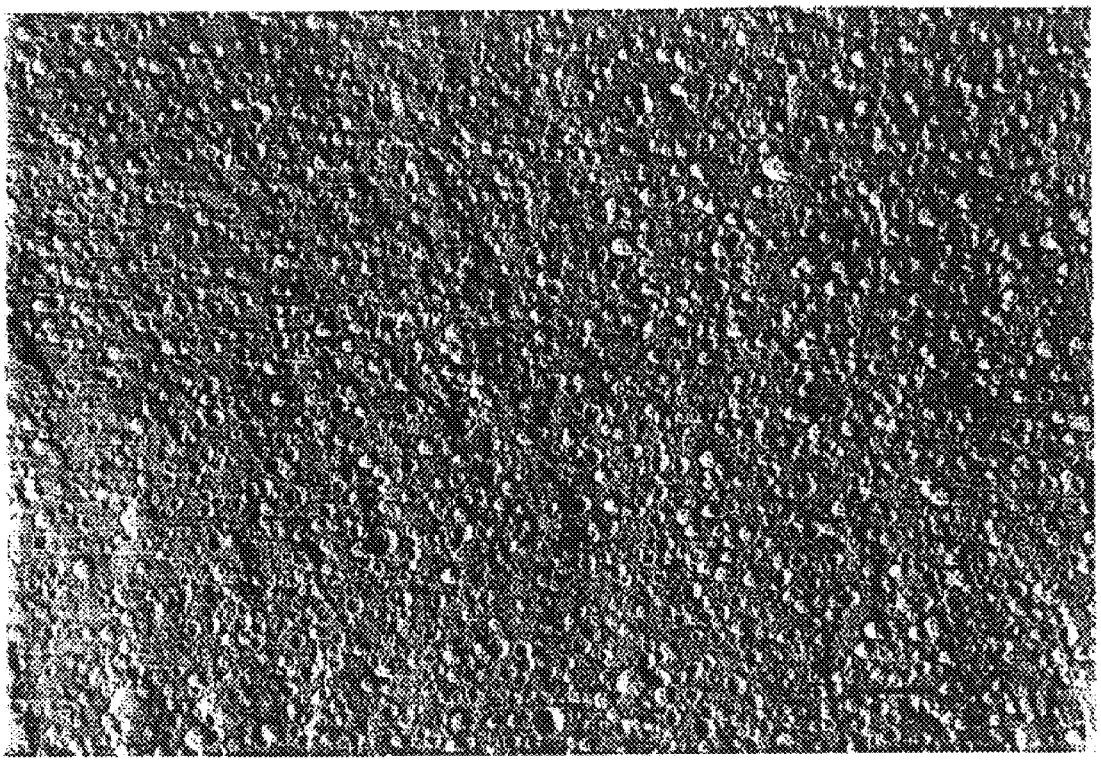
FIGS. 2A–D are freeze-fracture electron micrographs of DMPC SUVs with IL-2 prepared at the 0 hour (FIG. 2A), 0.5 hour (FIG. 2B), 6 hours (FIG. 2C) and 24 hours (FIG. 2D) time points. The reference bar equals 250 nm.

The present invention is directed to a novel method of producing MLCVs containing increased amounts of biologically active compounds. The method of the present invention produces MLCVs without the use of steps involving freeze-thawing, organic solvents or dehydration.

The first step of the present method involves direct hydration of a powdered lipid or mixture of lipids with the appropriate buffer in a temperature jacketed mixing vessel. Examples of appropriate buffers are phosphate buffered saline (PBS), acetate, or citrate with a pH between 2 and 12, preferably between 5 and 9. The hydration is preferably performed above the phase transition temperature of the highest melting lipid, and the hydrated suspension is mixed well. The next step involves size reduction, preferably to about 20–70 nm comprising SUVs and/or LUVs, but in any case, below about 400 nm, preferably below about 200 nm. This size reduction is performed using standard means, such as sonication, including bath or probe sonication, homogenization or extrusion. The size reduction is performed above the phase transition temperature of the highest melting lipid employed. If a mixture of lipids is used, the phase transition temperature of the highest melting lipid would be used. The resultant SUVs and/or LUVs are then sterile filtered (0.22 micron filter) into a sterile reaction vessel equipped with a mixing device and a temperature jacket to maintain the temperature above the phase transition temperature of the highest melting lipid. These LUVs are sufficiently deformable that larger sizes can squeeze through a sterile filter. To this vessel, one or more pharmaceutical(s), along with any other necessary excipients, such as, HSA, mannitol, and glycerol, are added through a sterilizing filter. This mixture is continually mixed while dropping the temperature to the phase transition temperature of the highest melting lipid, or preferably between its pretransition and main transition temperature. The incubation temperature may be below the pretransition temperature, below the subtransition temperature or above the main transition temperature. This mixture is then incubated for an extended period of time, but it can be incubated from minutes to hours, to possibly days, with optional continuous or intermittent mixing. During this time the SUVs and/or LUVs coalesce to form large vesicles, MLCVs, typically between 1000 and 5000 nm, but the MLCVs can be as small as about 100 nm in average diameter, and are multilamellar, with entrapped pharmaceuticals. The MLCVs of the present invention are unique structurally in that they possess a varying degree of partially coalesced vesicles in addition to numerous lamellae.

The preferred lipids are saturated lecithins, such as dimyristoyl phosphatidylcholine (DMPC); dipalmitoyl phosphatidylcholine (DPPC); distearoyl phosphatidylcholine (DSPC); saturated phosphatidylglycerols, such as dimyristoyl phosphatidylglycerol (DMPG), dipalmitoyl phosphatidylglycerol (DPPG), distearoyl phosphatidylglycerol (DSPG); saturated phosphatidic acids, saturated phosphatidylethanolamines or mixtures of the above lipids. Unsaturated lipids may also be employed, such as egg phosphatidylcholine (EPC) and dioleoyl phosphatidylcholine (DOPC).

The temperature of incubation may be at the pretransition temperature or the main transition temperature of the highest melting lipid used, although it could also be below the pretransition temperature or above the main transition temperature. The incubation can also be performed by cycling through a temperature range, such as between the pretransition and main transition temperatures.

Prior literature indicates that fusion of pure saturated phosphatidylcholines will occur below the phase transition of that lipid, and specifically below the pretransition. See Schmidt, C. F., Lichtenberg, D., and Thompson, T. E., *Biochemistry* 20:4792–4797 (1981); Larrabee, A. L. *Biochemistry* 18:3321–3326 (1979); Schullery, S. E., Schmidt, C. F., Felper, Tillack, T. W., and Thompson, T. E. *Biochemisty* 19:3919–3923 (1980); Petersen, N. O. and Chan 51 S. I., *Biochim. Biophys. Acta* 509:111–128 (1978); Wong, M., Anthony, F. H., Tillack, T. W., and Thompson, T. E. *Biochemistry* 21:4126–4132 (1982); McConnell, D. S. and Schullery, S. E., *Biochim. Biophys. Acta* 818:13–22 (1985); Gaber, B. P. and Sheridan, J. P. *Biochim. Biophys. Acta* 685:87–93 (1982). Fusion is typically to unilamellar vesicles of 70–95 nm. The fusion product is also capable of entrapping solute. See McConnell et al. Fusion at the phase transition was observed in one case to be similar to that obtained below the pretransition temperature. See Gaber and Sheridan (1982). The entrapment was not established and the kinetics of fusion was quite slow, taking up to weeks to occur.

The lipid used in the present method preferably should be saturated and may have any head group, such as phosphatidylcholine, phosphatidylglycerol, phosphatidic acid, phosphatidylethanolamine, or phosphatidylserine. In addition, mixtures of lipids with respect to both head group and chain length can be used. Mixtures with lipids that alone do not form liposomes, such as cholesterol or fatty acids, can be employed in this process. The lipid concentration should be between 1 mg/ml to 400 mg/mL, preferably for most applications between 100 mg/mL and 250 mg/mL. Saturated lecithins are preferred lipids for use in the present method.

The biologically active compound useful in the present invention can be any of the known biologically active compounds that can be entrapped in the liposomes and whose rate of diffusion out of the liposomes is not significantly greater than the rate of deterioration of liposomes in the body of the recipient. The biologically active compounds may have properties that enhance vesicle coalescence. These substances would act directly on the SUVs and/or LUVs by destabilizing their bilayer structure. A simple measurement of increased turbidity, such as illustrated in Example 1, permits ready identification of substances having this property of enhancing vesicle coalescence. The biologically active compounds can be selected from proteins, peptides, antigens, antibiotics, hormones, immunological activators, cytokines, lymphokines, polynucleotides, and other drugs. Specific examples of such compounds are IL-2, interferon, granulocyte-macrophage colony stimulating factor (GMCSF), insulin, growth hormone, epidermal growth factor, calcitonin, gentamicin, and antigens derived from bacteria, parasites, viruses or rickettsia, tumor antigens, allergens, poison or venom.

IL-2 is commercially available as recombinant T-cell growth factor (human IL-2, recombinant; T3267) or as a preparation derived from cultured rat splenocytes (TO892)

from Sigma Chemical Co. (St. Louis, Mo.). Recombinant IL-2 may also be obtained from Genzyme (Boston, Mass.) or R & D Systems (Minneapolis, Minn.). Other lymphokines known and available in the art also can be used in the present invention. These include interleukin-4 (IL-4), interleukin-6 (IL-6), interferon alpha and interferon gamma. It is envisioned that these lymphokines can be used alone, in sequence, or in combination, such as co-entrapment in the liposome (e.g., IL-2 and IL-6).

MLCVs according to the present invention are characterized by several features that distinguish them from MLVs made by prior art processes. One particularly salient feature is the highly uniform distribution of biologically active compound among the MLCVs. In many prior art MLV preparations, a high proportion, often about 50%, of the liposomes are substantially free of biologically active compound. By contrast, the MLCVs of the invention, when seen in freeze-fracture electron micrographs, normally have a low percentage of vesicles that are substantially free of biologically active compound, generally less than 30%, preferably less than 20%, often less than 10% and even less than 5% or even less than 2% of vesicles that are substantially free of biologically active compound as indicated by the absence of bulges. This property, in turn, permits a higher total entrapment of biologically active compounds by the MLCVs of the invention compared to prior art MLVs. A further feature, illustrated in Example 12 below, is that MLCVs according to the invention have a higher proportion of the biologically active material on the vesicle surface than prior art MLVs. In addition, the MLCVs of the invention permit a higher proportion of the entrapped biologically active compound to retain its biological activity compared to MLVs made by other methods.

The MLCVs of the invention contain in the range of 10–100% greater amount of biologically active compound than liposomes produced by the prior art methods using an organic solvent, a freeze-thawing step or a dehydration step. The MLCVs preferably contain at least 10% greater amount of biologically active compound than the prior art liposomes, preferably at least 20% greater amount biologically active compound, more preferably at least 30% greater amount biologically active compound, more preferably at least 40% greater amount biologically active compound, more preferably at least 50% greater amount biologically active compound, more preferably at least 80% greater amount biologically active compound, and more preferably at least 100% greater amount biologically active compound and even more than 100% greater amount biologically active compound.

Figure 2B:
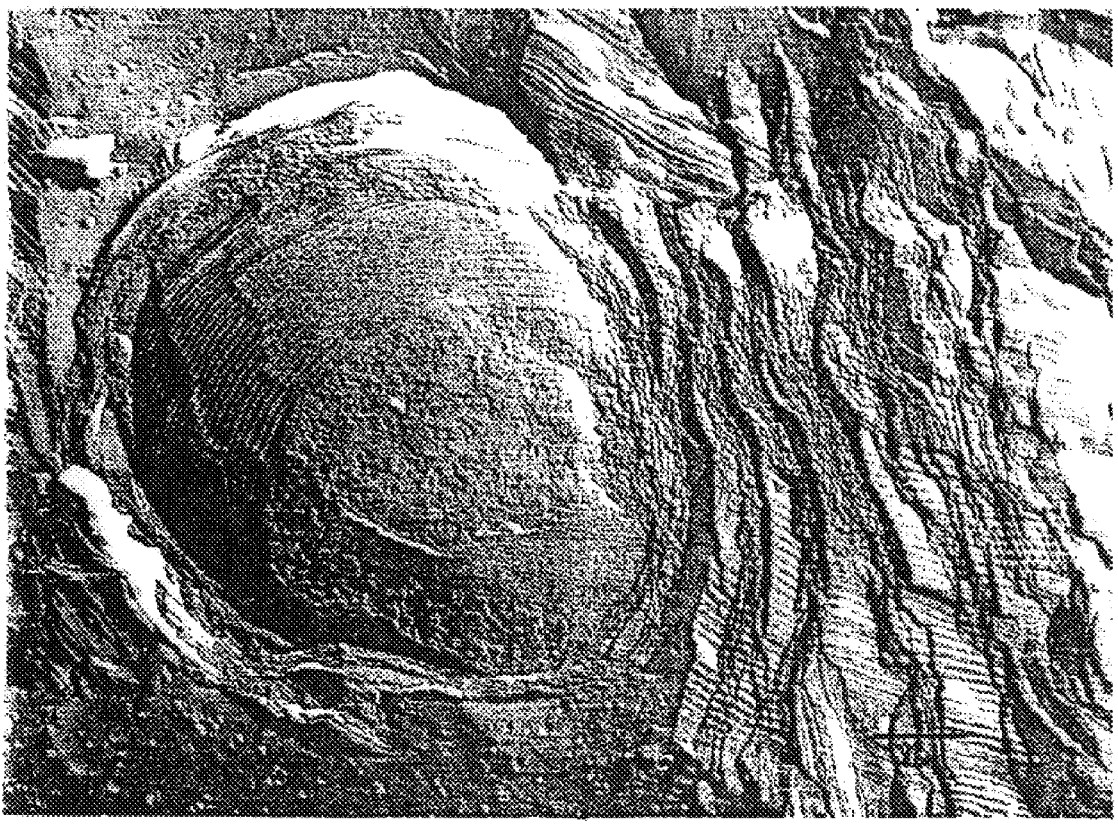

Many preparations of MLCVs according to the present invention contain partially coalesced SUVs and/or LUVs in the interior of the lamellae, a unique feature not seen in MLVs made by prior art methods. This can be seen in FIGS. 2B, 5 and 8B.

The present invention will be further described by reference to the following detailed examples. These examples are not intended to limit the present invention but rather are intended to illustrate specific aspects of the present invention.

EXAMPLES

Example 1

To determine the effect of temperature on IL-2 induced SUV coalescence, 200 mg of dimyristoyl phosphatidylcholine (DMPC) was hydrated in 1 mL of 1 mM phosphate buffer, pH 7, 0.9% saline, at 37° C., by vortexing producing MLCVs. This mixture was then sonicated in a bath sonicator until clear. The vesicle size of the resulting SUVs by PSS NICOMP, a submicron particle sizer was between 20 and 50 nm. The liposomes were sterile filtered for example using a 0.22 micron filter. To the filtered liposomes, 0.68 mg of IL-2 was added with and without 17 mg HSA. An increase in turbidity in time is observed, reaching a maximum at about 20 hours. This increase in turbidity is a reflection of aggregation, coalescence or fusion. FIG. 1A shows the results without HSA and FIG. 1B shows the results with HSA in the liposome preparations. Coalescence occurs at all the temperatures examined, with maximal effects at 19° C. between the pretransition and main transition temperatures of DMPC.

Example 2

Figure 2C:
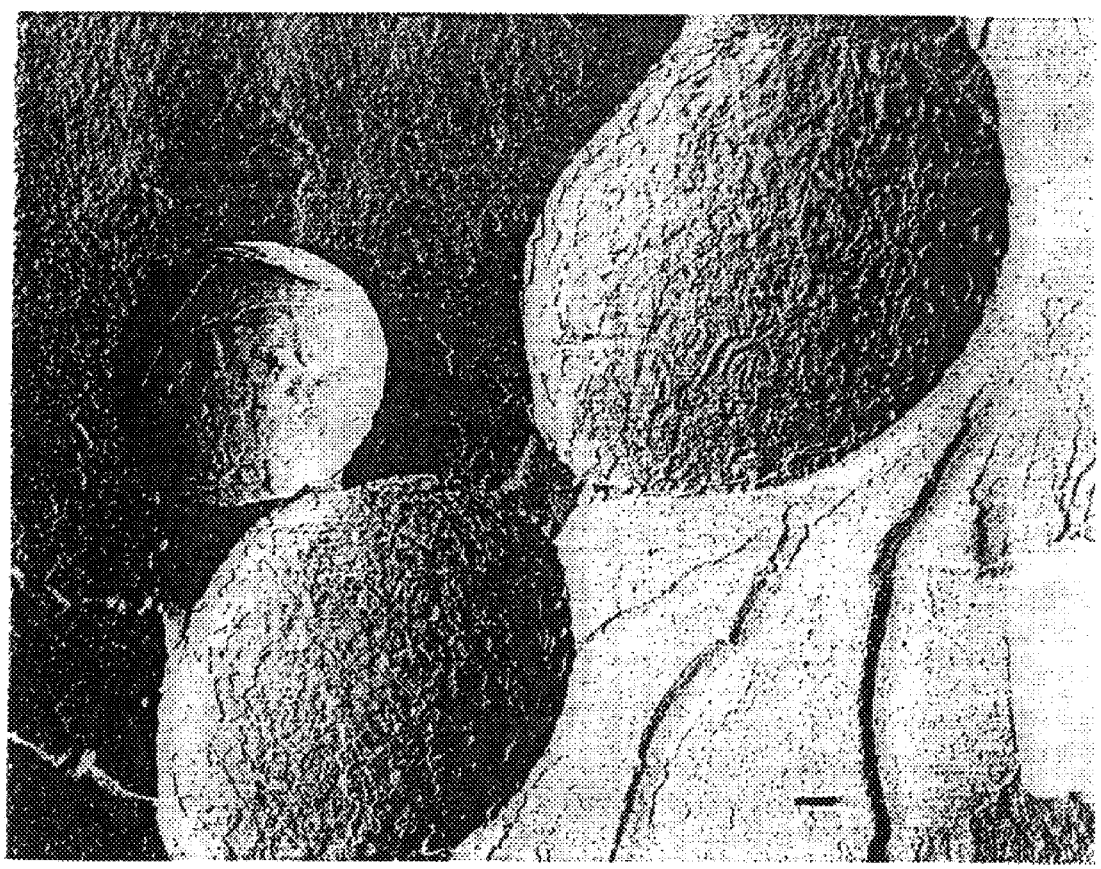
Figure 2D:
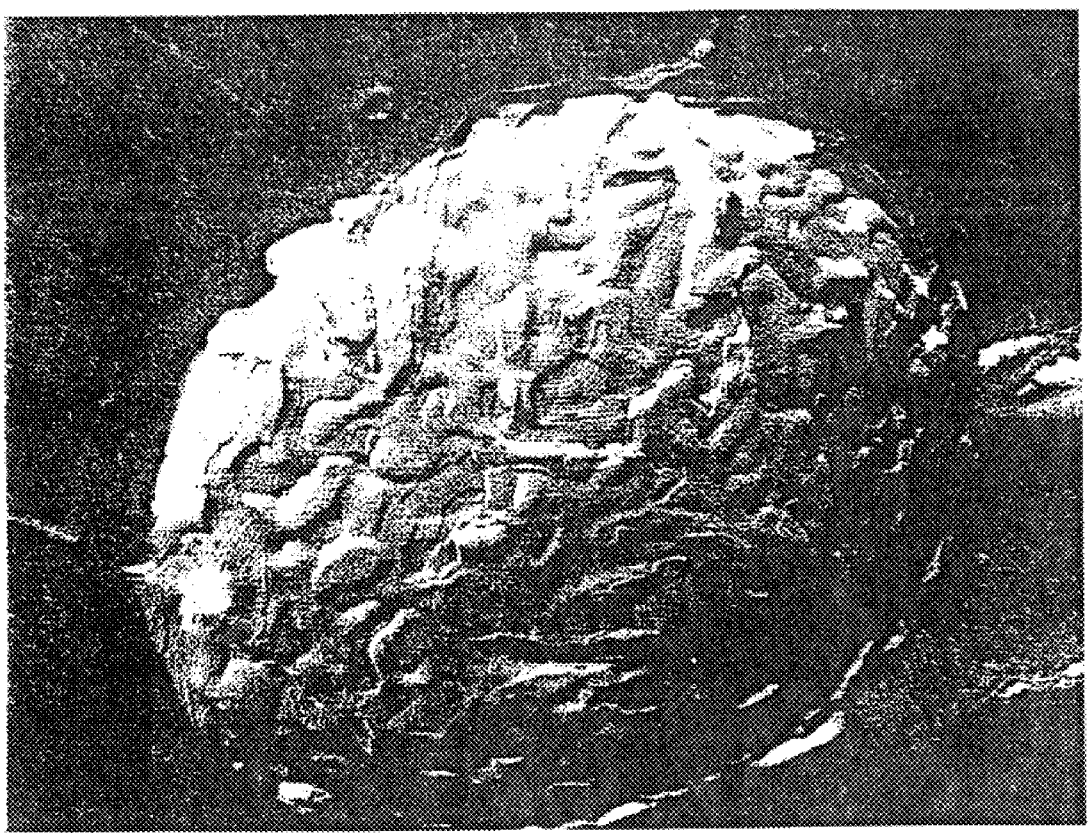

Freeze-fracture electron microscopy was employed to follow the kinetics of coalescence and to characterize the coalescence product (MLCV). DMPC SUVs obtained by bath sonication can be seen (FIG. 2A) to be homogeneous and around 25 nm in diameter. DMPC SUVs at 200 mg/mL were mixed with IL-2 (final mass ratio 250/1) at 19° C. and incubated at 19° C. At different times aliquots were rapidly frozen between thin copper planchets in preparation for freeze-fracture. At 30 minutes most of the replica looked like the control SUVs, but regions, as in FIG. 2B, revealed the start of SUV coalescence to MLCVs. Fully coalesced SUVs give rise to bilayer sheets with the characteristic $P_{\beta'}$ (ripple) phase typically seen in DMPC vesicles at this temperature. By 6 hours (FIG. 2C) large MLCVs have been formed. Note the large quantity of SUVs still present, indicating incomplete coalescence. By 24 hours large MLCVs are present with few background SUVs (FIG. 2D). These MLCVs contain bulges in the surface texture of the individual layers, characteristic of prior art DMPC MLVs with entrapped IL-2. However, the occurrence of bulges was uniform throughout the MLCVs, in contrast to MLVs, where many vesicles lack bulges and appear not to contain IL-2. The final size was large with a 2370 nm mean diameter (FIG. 3). The size was obtained using the Accusizer 770—Particle Sizing Systems (PSS).

Example 3

The MLCVs of Example 1 were analyzed for the presence of IL-2, using the cytotoxic T-lymphocyte line (CTLL) assay as described in Clin. Pharmacokinet. 27 (1) 19–31 (1994). Activity was $2.17 \times 10^6$ IU/mL, a 89% recovery with greater than 95% incorporation.

Example 4

Leakage experiments were performed to distinguish between vesicle fusion, where there is mixing of internal contents with minimal leakage, from vesicle coalescence where leakage of internal contents does occur. DMPC SUVs were formed in the presence of 10 mM 8-aminonapthalene-1,3,6-trisulfonic acid (ANTS) and 32 mM p-xylene-bis-pyridinium bromide (DPX). At these concentrations the DPX quenches the ANTS. The SUVs were washed by dialysis and incubated in the presence of IL-2 (DMPC/IL-2 at 250/1, mass ratio) at different temperatures. As can be seen in FIG. 4, leakage of the water-soluble ANTS and DPX occurs during the process of forming MLCVs, indicating that the process is primarily coalescence not fusion. Measurements were performed on a QM-1 spectrofluorimeter (Photon Technology International, South Brunswick, N.J.) with the excitation at 354 nm and the emission at 370–600 nm.

Example 5

Figure 5:
FIG. 5 is a freeze-fracture electron micrograph of a MLCV formed by incubating DMPC SUVs with IL-2 (mass ratio 25/1). The reference bar equals 250 nm.

MLCVs were formed by incubating DMPC SUV with IL-2 at a DMPC/IL-2 mass ratio of 25/1. The incubation was performed at 19° C. and for two days. As can be seen in FIG. 5, the MLCVs contain SUVs within the lamellae that have not completely coalesced. This illustrates the earlier statement that MLCVs of the invention are unique structurally in that they possess a varying degree of partially coalesced vesicles in addition to numerous lamellae.

Example 6

Figure 6:
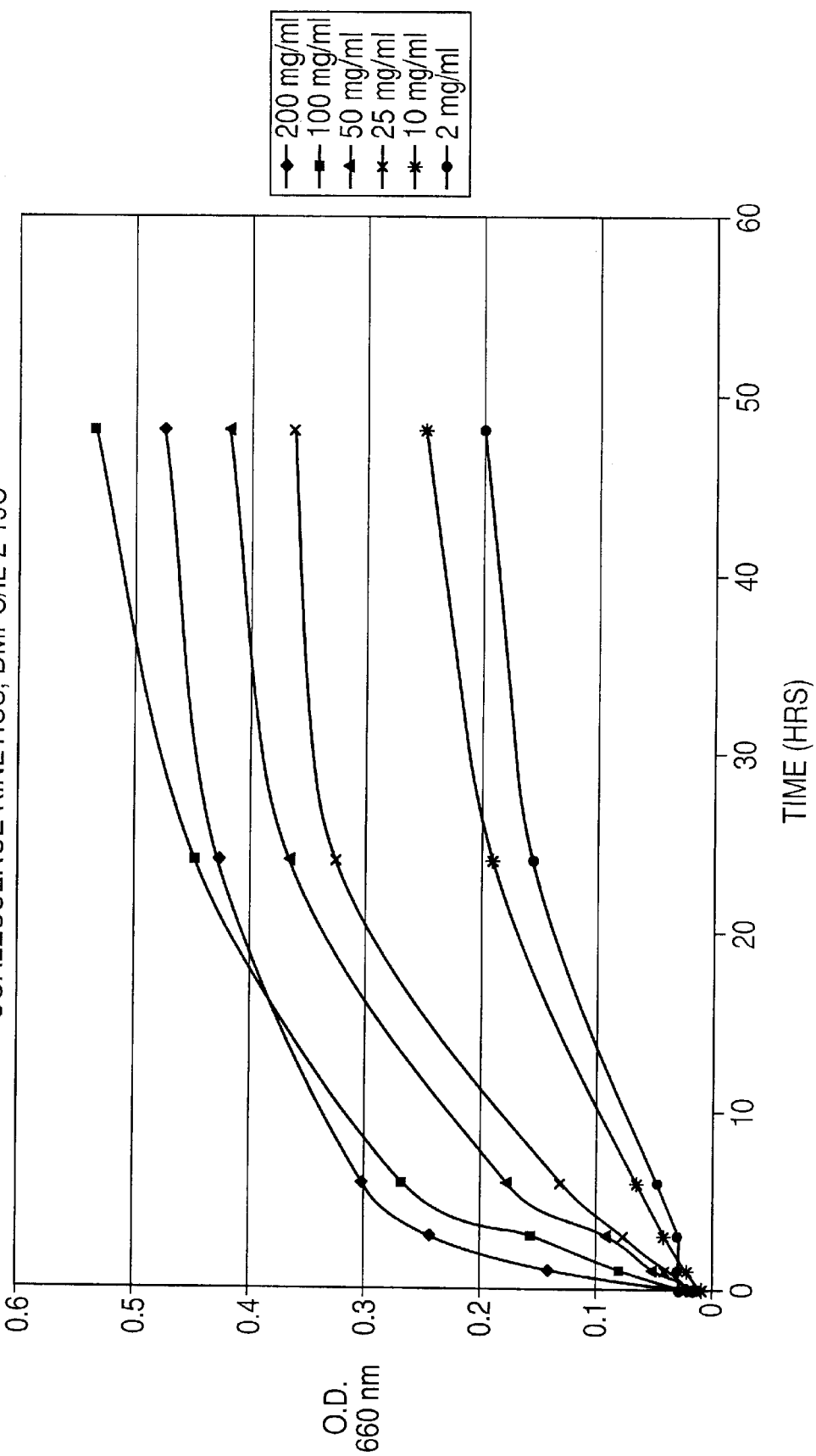
FIG. 6 is a graphical depiction of the rate of DMPC SUV coalescence for the varying lipid concentrations from 200 mg/mL to 2 mg/mL.

The effect of concentration of DMPC on the rate of coalescence was observed for a range of 200 mg/mL to 2 mg/mL, as shown in FIG. 6. The mass ratio of DMPC/IL-2 was kept constant at 300/1. All samples were diluted to 2 mg/mL prior to measurement. Note the gradual decrease in the rate and extent of coalescence as the concentration of components decreases. The coalescence, as measured by turbidity, reaches a plateau at about 24 hours. This example shows the range of lipid concentrations that can be employed for the MLCV process.

Example 7

The effect of the DMPC/IL-2 on the rate of coalescence for the range of 50/1 to 2000/1 (mass ratio) is shown in FIG. 7. The coalescence as measured by the amount of lipid in the supernatant after centrifugation at 39,000 g for 30 minutes, drops off rapidly with increasing DMPC/IL-2 ratio. This defines the optimal range for coalescence to be at a DMPC/IL-2 mass ratio between 50/1 and 450/1.

Example 8

Figure 8A:
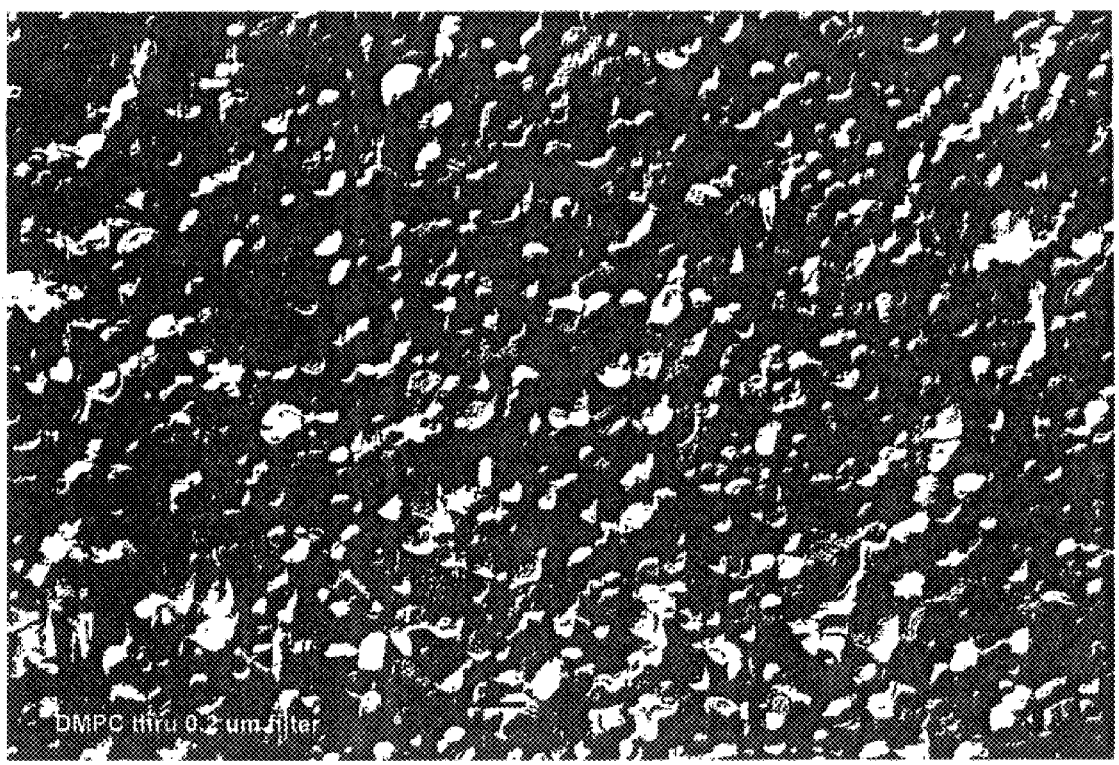
FIGS. 8A and 8B are freeze-fracture electron micrographs of DMPC LUVs at 130 nm before and after a 24 hour incubation at 19° C. with IL-2. The reference bar equals 250 nm.
Figure 8B:
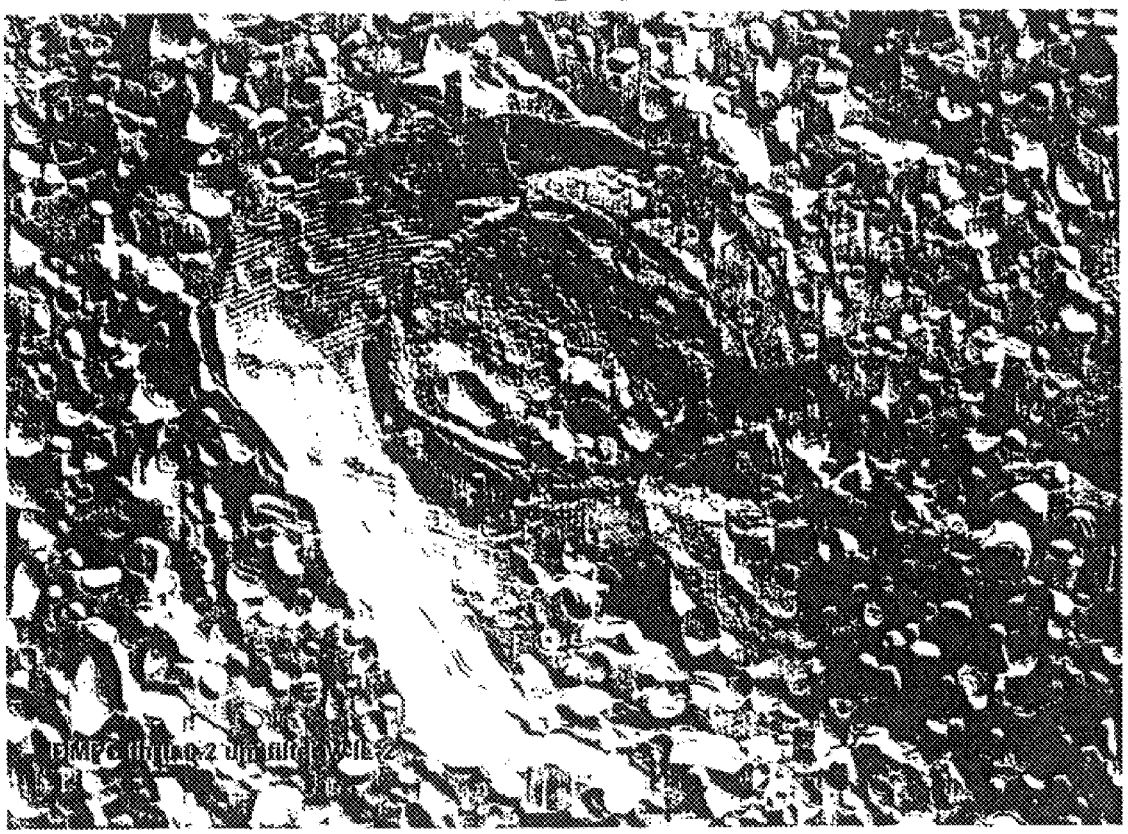

To test the size limitation of the coalescence process, LUVs of DMPC were made by extrusion through polycarbonate filters (Nuclepore, Corning) in an extrusion device (Lipex, Vancouver, BC, Canada). The filters employed were 0.1 and 0.2 microns giving rise to 89 nm and 130 nm LUVs, respectively. FIG. 8A shows an electron micrograph of the 130 nm vesicles. After 24 hours incubation at 19° C., many LUVs remained, although MLCVs were also present (FIG. 8B). These figures reveal the presence of incompletely or partially coalesced LUVs within the structure of the MLCV. Similar results were obtained with the 89 nm LUVs.

Example 9

This experiment shows the scale-up of the coalescence of DMPC SUV in the presence of IL-2 and HSA. A three liter vessel was used to make a 750 mL batch. SUVs were made from MLVs using a Microfluidics homogenizer. The mixture was incubated overnight between the pre transition and main transition temperatures of DMPC. The resultant liposomes were large, with a 2600 nm mean diameter and an activity of $1.08 \times 10^6$ IU/mL (68% recovery) and 98% incorporation. This product was stable with respect to IL-2 activity for greater than nine months.

Example 10

The use of lipids other than DMPC was also employed in the MLCV coalescence process. Specifically, the effect of chain length, chain unsaturation, and charge were examined. The % coalescence is the total lipid minus the lipid remaining in the supernatant following centrifugation at 39,000 g for 30 minutes. Table 1 illustrates the ability of other lipids to entrap IL-2 by the MLCV coalescence method, although not as efficiently as DMPC. Light microscopy reveals large liposomes for both the DPPC and DMPC/DMPG products, but large aggregates for the EPC product. Closer examination of the EPC SUVs product by freeze-fracture electron microscopy reveals some small MLCVs less than a micron (1000 nm) in diameter with many unfused SUVs. These MLCVs contain the bulges indicative of an irregular interbilayer spacing as observed for DMPC MLCVs formed by this process. Thus, this effect is not restricted to saturated lipids.

TABLE 1

Different Lipids Employed in the SUV Coalescence Process

| Lipid (# of experiments) | incubation T (° C.) | % recovery of IL-2 bioactivity | % incorp. of IL-2 bioactivity | % coalescence |
|---|---|---|---|---|
| DMPC (2) | 4 | 37 | 93 | 71 |
| DMPC (2) | 19 | 59 | 97 | 94 |
| DMPC | 23 | 64 | 93 | 34 |
| DMPC | 38 | 43 | 88 | 25 |
| DPPC | 4 | 70 | 73 | 88 |
| DPPC | 19 | 56 | 73 | 82 |
| DPPC | 38 | 55 | 83 | 93 |
| DPPC | 55 | 11 | 88 | 97 |
| DMPC/DMPG 9:1 (1) | 19 | 66 | 97 | |
| DMPC/DMPG 5:1 | 19 | 107 | 94 | |
| DMPC/Chol. 2:1 | 4 | 37 | 69 | |
| DMPC/Chol. 2:1 | 19 | 43 | 63 | |
| DMPC/Chol. 2:1 | 23 | 38 | 38 | |
| DMPC/Chol. 2:1 | 38 | 64 | 47 | |
| DOPC | 4 | 40 | 82 | |
| DOPC | 19 | 31 | 81 | |
| EPC | 4 | 77 | 12 | |
| EPC | 19 | 70 | 24 | |
| EPC | 38 | 8 | 45 | |
| EPC/Chol, 2:1 | 4 | 62 | 49 | |
| EPC/Chol, 2:1 | 19 | 69 | 28 | |
| EPC/Chol, 2:1 | 38 | 4 | 45 | |

Example 11

The use of the present method to entrap pharmaceuticals other than IL-2, such as tumor antigens, is demonstrated. DMPC SUVs were incubated overnight in the presence of IL-2 and either IgG or IgM isolated from lymphoma patients. The initial concentration of lipid was varied between 40 mg/mL and 185 mg/mL. Samples were incubated overnight at 19° C. and then frozen for storage until assayed. Results shown below in Table 2 indicate good incorporation of antigen and IL-2. The data illustrate that a different protein can be entrapped in the MLCVs and that this protein does not interfere with the coalescence process. It also is noted that samples that are frozen for storage give substantially the same results before and after freezing.

TABLE 2

Incorporation of Antigens and IL-2 into MLCVs

| Lipid Concentration | Immunoglobulin Incorporation | | IL-2 Incorporation | |
|---|---|---|---|---|
| (mg/mL) | (μg/mL) | % | ($\times 10^6 \times$ IU/mL) | % |
| Immunoglobulin M | | | | |
| 40 | 401 | 5.3 | 2.2 | 85 |
| 80 | 385 | 13.2 | 1.9 | 80 |

TABLE 2-continued

Incorporation of Antigens and IL-2 into MLCVs

| Lipid Concentration (mg/mL) | Immunoglobulin Incorporation | | IL-2 Incorporation | |
|---|---|---|---|---|
| | (µg/mL) | % | (×10⁶ × IU/mL) | % |
| 158 | 371 | 22.2 | 3.0 | 83 |
| 185 | 266 | 31.1 | 1.8 | 90 |
| Immunoglobulin G | | | | |
| 40 | 130 | 4.6 | 1.5 | 86 |
| 80 | 155 | 6.8 | 1.9 | 78 |
| 158 | 146 | 19.7 | 2.4 | 88 |
| 185 | 74 | 16.5 | 1.8 | 94 |

Example 12

MLCVs were prepared with and without HSA as in Example 1 employing a 24 hour incubation at 19° C. MLVs containing IL-2 were prepared with and without HSA by the method of Anderson and Sorenson (1994), hereinafter referred to as the MLV method. The MLCVs and MLVs were then examined for surface IL-2. The primary antibody, rabbit anti-human IL-2 (Endogen), was added to washed MLCVs or MLVs at 6 µg/mL, and then washed on 0.2% milk to remove unbound antibodies, to which goat anti-rabbit IgG-biotin (Southern Biotechnology) was added. Following incubation for 30 minutes at 4° C., the MLCVs and MLVs were again washed in skimmed milk. Finally streptavidin-europium (Eu) (1/1000 dilution) (Wallac) was added, followed by a 5 minute incubation at 4° C. and washing with 0.2% skimmmed milk. Enhance solution (Wallac) was added and the bound Eu was determined by time resolved fluorimetry (Wallac 1234 Delfia Research Fluorometer, Gaithersburg, Md.).

As can be seen in FIG. 9, a greater surface labeling is obtained for the MLCVs, particularly without HSA. High levels of antibody binding to the liposome surface by the MLV method requires HSA during processing. This result also could indicate a different surface IL-2 orientation for MLCVs compared to MLVs, that is process dependent. IL-2 activity as measured by CTLL revealed a recovery of activity for the MLCVs of greater than 90% while the MLVs revealed a recovery of activity of around 50%. Thus the MLCV process of the present invention yields liposomes with a higher surface IL-2 and total IL-2 content without the need for HSA compared to liposomes produced by the MLV method.

REFERENCES

1. Poznansky and Juliano, *Pharmacol. Rev.* 36 , 277–336 (1984).
2. B. E. Ryman et al., *Essays in Biochemistry*, 16, 49 (1980).
3. Gregoriadis and Allison, eds., *Liposomes in Biological Systems*, John Wiley & Sons, New York (1980) at pages 153–178.
4. G. Lopez-Berestein, *Ann. Int. Med.*, 105, 130 (1985).
5. Hsieh et al., *Transplantation Proceedings*, Vol. XVII, 1397–1400 (1985).
6. Rahman et al., *Cancer Res.*, 42, 1817 (1982).
7. Forssen et al., *Cancer Res.*, 43, 546 (1983).
8. Bangham et al. (1974) *In Methods in Membrane Biology* (Korn, E., ed.), pp 1–68, Plenum Press, N.Y.
9. Gingell, D. and Ginsberg, L. (1978), In: *Membrane Fusion* (Poste, G. & Nicolson, G. L., eds.), pp.791–833, Elsevier/North-Holland Biomedical Press, NY.
10. Szoka, F. (1987) In: *Cell Fusion* (Sowers, A. E., ed.), pp. 209–240, Plenum Press, NY.
11. Nir, S., Wilschut, J. and Bentz, J. (1982), *Biochim. Biophys. Acta* 688:275–278.
12. Jackson (1981), *Drug Med. Disp.* 9: 535–540.
13. Anderson, P. M. and Sorenson, M. A. (1994), *Clin. Pharmacokinet.* 27 (1): 19–31.
14. Schmidt, C. F., Lichtenberg, D., and Thompson, T. E. (1981), *Biochemistry* 20:4792–4797.
15. Larrabee, A. L. (1979), *Biochemistry* 18:3321–3326.
16. Schullery, S. E., Schmidt, C. F., Felper, Tillack, T. W., and Thompson, T. E. (1980) *Biochemisty* 19:3919–3923.
17. Petersen, N. O. and Chan 51 S. I. (1978), *Biochim. Biophys. Acta* 509:111–128.
18. Wong, M., Anthony, F. H., Tillack, T. W., and Thompson, T. E. (1982), *Biochemistry* 21:4126–4132.
19. McConnell, D. S. and Schullery, S. E. (1985), *Biochim. Biophys. Acta* 818:13–22.
20. Gaber, B. P. and Sheridan, J. P. (1982), *Biochim. Biophys. Acta* 685:87–93.

What is claimed is:

1. A method for producing multilamellar coalescence vesicles (MLCVs) containing a biologically active compound, said method comprising:
    incubating small unilamellar vesicles (SUVs), large unilamellar vesicles (LUVs) or mixture thereof with at least one biologically active compound in an aqueous solution at a temperature above the temperature of the pretransition of the lipid component for a time sufficient to form MLCVs containing said at least one biologically active compound;
    wherein said method is performed without the use of an organic solvent, a freeze-thawing step or a dehydration step.

2. The method of claim 1, wherein said method further comprises sterile filtering the SUVs, LUVs or combination thereof prior to mixing the SUVs, LUVs or mixture thereof with the biologically active compound or compounds.

3. The method of claim 1, wherein said biologically active compound is a protein or peptide having coalescence properties.

4. The method of claim 3, wherein said biologically active compound is a cytokine.

5. The method of claim 4, wherein said cytokine is interleukin-2 (IL-2).

6. The method of claim 1, wherein a mixture of at least two biologically active compounds are incorporated into said MLCVs.

7. The method of claim 6, wherein each component of said mixture of biologically active compounds is selected from the group consisting of an immunoglobulin, a tumor antigen, a cytokine and a polynucleotide.

8. Multilamellar coalescence vesicles (MLCVs) containing at least one biologically active compound, produced by the method of claim 1.

9. The MLCVs of claim 8, wherein said MLCVs have an average diameter of at least about 100 nm.

10. The MLCVs of claim 8, wherein said MLCVs have an average diameter of about 1000–5000 nm.

11. The MLCVs of claim 8, wherein said MLCVs contain between about 10–100% greater amount of biologically active compound than liposomes produced by methods using an organic solvent, a freeze-thawing step or a dehydration step.

12. The MLCVs of claim 8, wherein said MLCVs contain at least 20% greater amount of biologically active compound than liposomes produced by methods using an organic solvent, a freeze-thawing step or a dehydration step.

13. The MLCVs of claim 8, wherein said MLCVs contain at least 50% greater amount of biologically active compound than liposomes produced by methods using an organic solvent, a freeze-thawing step or a dehydration step.

14. The MLCVs of claim 8, wherein said MLCVs contain at least 100% greater amount of biologically active compound than liposomes produced by methods using an organic solvent, a freeze-thawing step or a dehydration step.

15. MLCVs comprising lipid and at least one biologically active compound, wherein less than 30% of the vesicles are substantially free of biologically active compound.

16. The MLCVs of claim 15, wherein less than 20% of the vesicles are substantially free of biologically active compound.

17. the MLCVs of claim 15, wherein less than 10% of the vesicles are substantially free of biologically active compound.

18. The MLCVs of claim 15, wherein less than 5% of the vesicles are substantially free of biologically active compound.

19. The MLCVs of claim 15, wherein less than 2% of the vesicles are substantially free of biologically active compound.

20. MLCVs comprising lipid and at least one biologically active compound, wherein at least a portion of the vesicles contain partially coalesced SUVs and/or LUVs in the interior of the lamellae.

* * * * *